United States Patent
Reiderman et al.

(10) Patent No.: US 6,452,388 B1
(45) Date of Patent: Sep. 17, 2002

(54) METHOD AND APPARATUS OF USING SOFT NON-FERRITIC MAGNETIC MATERIAL IN A NUCLEAR MAGNETIC RESONANCE PROBE

(75) Inventors: Arcady Reiderman, Houston, TX (US); David R. Beard, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/605,463

(22) Filed: Jun. 28, 2000

(51) Int. Cl.$^7$ .................................................. G01V 3/00
(52) U.S. Cl. ..................... 324/303; 324/318; 324/322; 324/309
(58) Field of Search ................................ 324/318, 319, 324/321, 322, 303

(56) References Cited

U.S. PATENT DOCUMENTS

| | | | |
|---|---|---|---|
| 4,629,986 A | 12/1986 | Clow et al. ................. 324/303 |
| 5,376,884 A | 12/1994 | Sezginer ..................... 324/303 |
| 5,486,761 A | 1/1996 | Sezginer ..................... 324/303 |
| 5,606,260 A | 2/1997 | Giordano et al. ........... 324/339 |
| 5,644,231 A | 7/1997 | Wignall ...................... 324/303 |
| 5,710,511 A | * 1/1998 | Taicher et al. .............. 324/303 |
| 5,712,566 A | 1/1998 | Taicher et al. .............. 324/303 |
| 5,757,186 A | 5/1998 | Taicher et al. .............. 324/303 |
| 6,018,243 A | * 1/2000 | Taicher et al. .............. 324/303 |
| 6,069,479 A | * 5/2000 | Taicher et al. .............. 324/309 |
| 6,215,304 B1 | 4/2001 | Slade ......................... 324/303 |
| 6,326,786 B1 | * 12/2001 | Kruspe ....................... 324/303 |
| 6,348,792 B1 | * 2/2002 | Beard et al. ................ 324/303 |

FOREIGN PATENT DOCUMENTS

| EP | WO 0002/01256 | * 1/2002 |
|---|---|---|
| GB | 2141236 A | 12/1984 |

* cited by examiner

Primary Examiner—Edward Lefkowitz
Assistant Examiner—Tiffany A. Fetzner
(74) Attorney, Agent, or Firm—Madan, Mossman & Sriram, P.C.

(57) ABSTRACT

The present invention provides a novel use of a powdered high saturation flux density soft magnetic material as a NMR probe core material. The probe structural geometry facilitates the use of powdered material, which has a relatively low magnetic permeability.

27 Claims, 6 Drawing Sheets

METHOD AND APPARATUS OF USING SOFT NON-FERRITIC MAGNETIC MATERIAL IN A NUCLEAR MAGNETIC RESONANCE PROBE

FIELD OF THE INVENTION

The present invention is related to the field of nuclear magnetic resonance ("NMR") sensing apparatus. More specifically, the invention is related to a NMR well logging apparatus having a powdered soft magnetic material core as a flux concentrator for sensing NMR properties within earth formations adjacent a wellbore.

DESCRIPTION OF THE RELATED ART

NMR well logging instruments can be utilized for determining properties of earth formations including: the fractional volume of pore space, the fractional volume of mobile fluid filling the pore space and other petrophysical parameters. An NMR well logging instrument typically contains a permanent magnet to generate a static magnetic field in adjacent earth formations. The NMR well logging instrument typically includes a transmitting antenna assembly positioned near the magnet. The transmitting antenna assembly is shaped so that a pulse of radio frequency (RF) power conducted through the antenna assembly induces a RF magnetic field in the adjacent earth formation. The induced RF magnetic field is generally orthogonal to the static magnetic field, thereby creating appropriate conditions for NMR excitation in the formation.

Following the RF antenna pulse, voltages representative of NMR conditions in the formation are induced in the receiving antenna. In particular, these voltages represent precessional rotation of hydrogen or other nuclei spin axes about the static magnetic field generated by the NMR well logging tool. NMR apparatus designs typically use the same antenna for transmitting and receiving along with de-coupling, receiving and protection circuitry.

There are various known NMR well logging instruments proposed and/or implemented for measuring NMR properties of substances, in particular, the properties of earth formations. One type of NMR instrument is described in U.S. Pat. No. 4,710,713 ('713), by Taicher et al. Another type of NMR instrument is described in U.S. Pat. No. 4,350,955 ('955), by Jackson et al. Both of these NMR instruments represent early designs of well logging NMR instruments with the main focus on the magnet assembly. No provision was made in these early designs for the use of a soft magnetic material in the NMR probe for improving the efficiency of the RF antenna.

It was recognized in more recent NMR well logging tool designs that a soft magnetic material can be utilized as a magnetic flux concentrator to increase efficiency of generating and receiving RF signals. For example, the NMR well logging instruments using ferrite material as an essential element of the design are described in U.S. Pat. No. 5,712,566 ('566), by Taicher et al., in U.S. Pat. No. 5,644,231 ('231) by A. H. Wignall, in UK Patent Application GB 2 141 236 ('236) by A to H. Clow, et al. and in U.S. Pat. No. 5,376,884 ('884) by A. Sezginer.

All prior designs known to the present inventors, however, explicitly or implicitly suggest ferrite as the soft magnetic material satisfying the requirements of high permeability and negligible RF losses. Ferrite materials, however, suffer from a relatively low saturation flux density, typically in the range of 0.3–0.4 T. This relatively low saturation flux density results in core saturation when the ferrite core is placed near the NMR probe permanent magnet. NMR probe core saturation results in reduction of the core magnetic permeability which tends increase core sensitivity to temperature variations. A sintered ferrite material core tends to generate magnetostrictive ringing in a strong static or RF magnetic field. Elimination of this parasitic magnetostrictive ringing signal increases the complexity and cost of NMR antenna design.

A common limitation of the '231, '566, '884, and '236 patent designs is the necessity of finding or creating a substantially zero magnetic field in a region where the soft ferrite material can be positioned to avoid saturation. For example, the apparatus disclosed in the '231 patent provides a soft magnetic ferrite material loaded in the antenna coil (a so called half-coax antenna). As described in the '231 patent, the effectiveness of the ferrite material is substantially reduced by the strong magnetic field of the permanent magnet. The structure of the '231 patent compensates for this reduction in effectiveness by providing a magnetic shield around the ferrite region. The shield comprises a shell of soft magnetic steel, which effectively provides a shunt path for static magnetic field in the region of the antenna. Implicitly, the steel shell is not saturated due to its sufficient saturation flux density and cross-sectional area. The necessity of creating a region of substantially zero static magnetic field places a serious constraint on the design of NMR probes. In particular it places limitations on the antenna core size, thereby reducing the efficiency of the antenna. Thus only a region very close to such a NMR antenna can be effectively analyzed.

Thus, there is a need for a NMR probe core material that overcomes the limitations of prior art discussed above.

SUMMARY OF THE INVENTION

The present invention provides a novel use of a powdered high saturation flux density soft magnetic material as a NMR probe core material. The probe structural geometry facilitates the use of powdered material, which has a relatively low magnetic permeability. In accordance with a preferred embodiment of the present invention a nuclear magnetic resonance sensing apparatus is provided, comprising a magnet for inducing a static magnetic field in materials to be analyzed; an antenna assembly for inducing a radio frequency magnetic field within the materials and for detecting nuclear magnetic resonance signals from the materials, the antenna comprising at least one magnetic core formed from a powdered soft magnetic material having high saturation flux density and a non-conductive bonding agent.

The magnetic core has dimensions related to the direction of RF magnetic field and to magnetic permeability of the powdered soft material. In particular, an effective demagnetizing factor of the magnetic core in the direction of the radio frequency magnetic field substantially exceeds the inverse magnetic permeability of the powdered soft magnetic material. As applied to NMR oil-well logging the present invention provides a permanent magnet and an antenna elongated in the direction of bore-hole, the permanent magnet and the antenna assembly disposed adjacent one another. The dipole magnetic moments of the antenna and the magnet are perpendicular to one another the direction of elongation. A variety of embodiments of this type of structure are presented.

There are numerous advantages associated with use of the preferred powdered soft magnetic core material and NMR probe structure of the present invention. The NMR powdered soft magnetic probe core material and probe structure provided by the present invention enables optimization of RF antenna efficiency in NMR probes without incurring the practical limitations of ferrite NMR probes. Ferrite NMR probe cores are less efficient than the preferred probe of the present invention, due to potential saturation of the ferrite by the static magnetic field of NMR probe permanent magnets. The core material of the present invention is not saturated by the NMR probe magnetic field because of the high saturation flux density of the preferred core material. Therefore, the preferred core material can be placed close to a strong permanent magnet in a NMR probe without saturating the soft magnetic material and diminishing the efficiency of the RF antenna in the NMR probe.

In a preferred embodiment, the RF magnetic flux is concentrated in the preferred core, thus, the conductivity of the probe permanent magnet does not reduce RF antenna efficiency of the probe, thereby enabling utilization of the strongest available commercial magnets. The preferred powdered core material reduces or eliminates magnetostrictive ringing by virtue of the particulate structure of the preferred material. The magnetic particle size of the preferred core material (powder) is substantially smaller than the minimum wavelength for acoustic excitation associated with magnetostrictive ringing. Moreover, the preferred probe antenna core magnetic and electrical characteristics are more stable than ferrite core characteristics in the presence of temperature variations.

Further features and advantages of the invention will become more readily apparent from the following detailed description, when taken in conjunction with the accompanying drawings.

The application is best understood with reference to the following drawings wherein like numbers in different figures refer to like components.

DETAILED DESCRIPTION OF A PREFERRED EMBODIMENT

Figure 1:
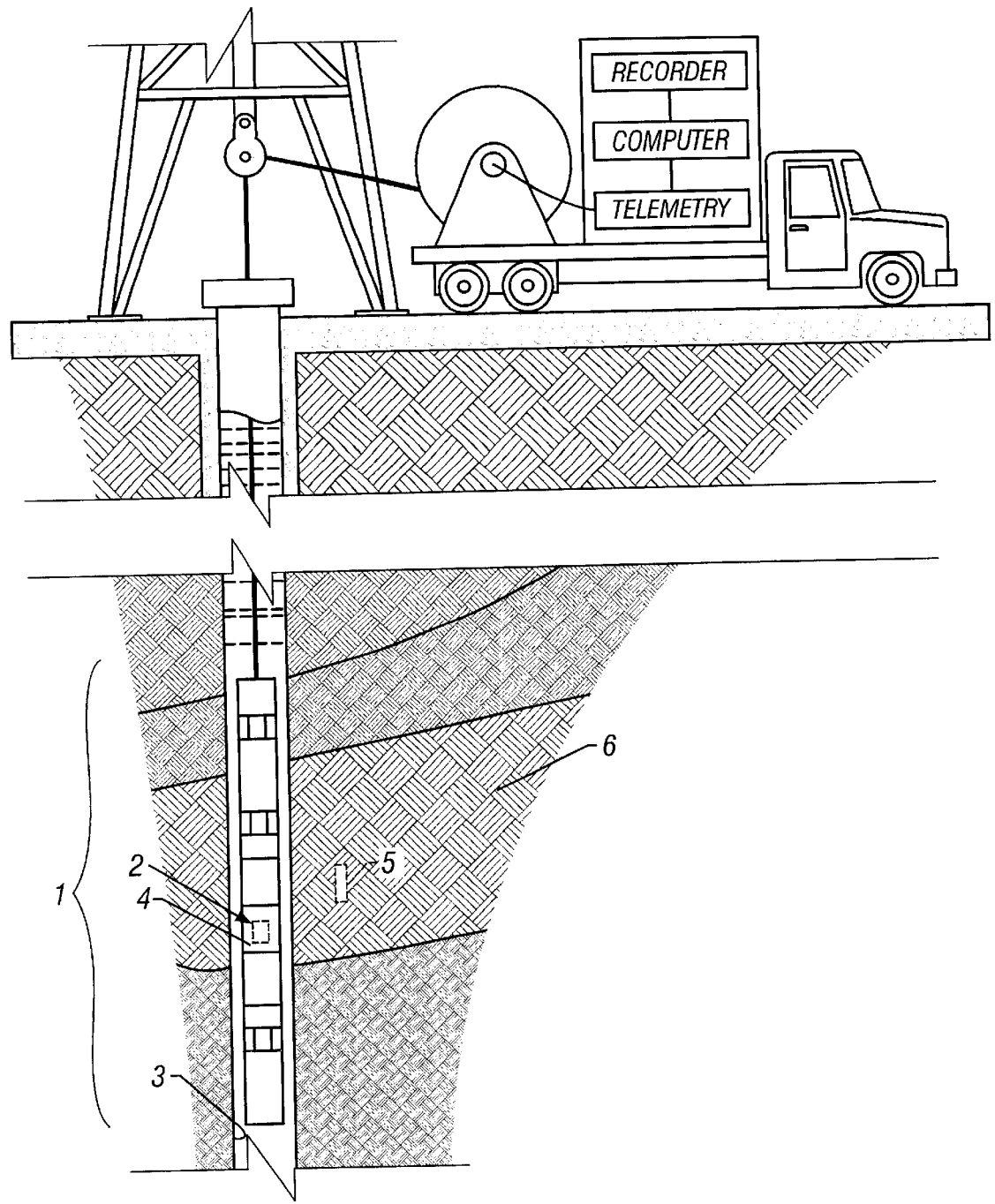
FIG. 1 is an illustration of a typical NMR tool deployed in a bore hole.

FIG. 1, illustrates well logging tool string 1 having an NMR probe 2, having antenna assembly 4 deployed in bore hole 3. The NMR probe sends magnetic pulses into and receives signals from region of investigation 5 in formation 6. FIG. 1 is shown for purposes of showing an example of the orientation of a tool utilizing the present invention and is not intended to limit the use of the present invention to a particular application or orientation.

Figure 2:
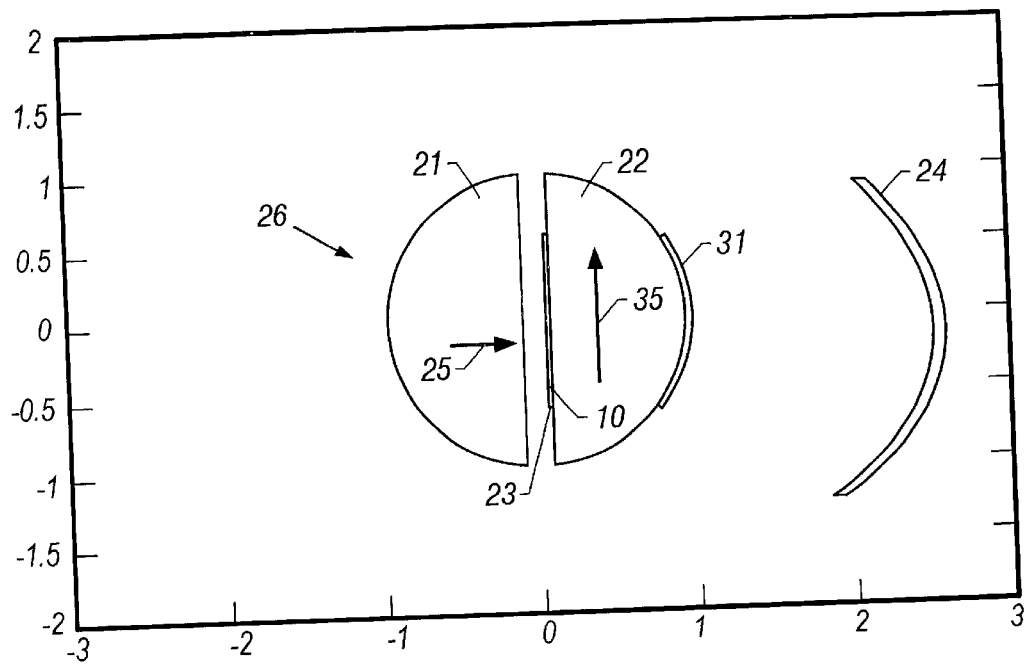
FIG. 2 is a cross-sectional view of a preferred embodiment of the present invention illustrating the geometry of a preferred NMR probe using the preferred powdered soft magnetic material of the present invention.

FIG. 2 illustrates a cross section of a preferred embodiment of the probe of the present invention, taken perpendicular to axis of elongation. The preferred embodiment of FIG. 2, comprises a probe 2, moveable through a bore hole 3 for measuring nuclear magnetic resonance (NMR) properties of a formation 6 surrounding the bore hole. The preferred probe comprises an elongated permanent magnet 21, having an axis of elongation extending parallel to the axis of elongation of the probe 2 and parallel to the longitudinal axis of the bore hole 3. The axes of elongation are perpendicular to plane of FIG. 2. Permanent magnet 21 has magnetic dipole moment 25 perpendicular to the axes of elongation. Preferred antenna assembly 10 has an axis of elongation generally parallel to the axis of the magnet 21. The preferred antenna assembly 10 comprises soft magnetic core 22 and flat wires 23 and 31. Core 22 is preferably comprised of the preferred powdered soft magnetic material such as the commercially available MICROMETALS™ or FLUXTROL™ iron powder materials and preferably comprises a ferromagnetic metal powder combined with an organic non-conductive binder, such as an epoxy resin. The particle size of the powder is small enough to appear transparent to the RF magnetic field. In the 0.5–1.0 MHz frequency range, the preferred non-ferrite soft magnetic material exhibits acceptable RF losses, thereby causing negligible deterioration of the NMR antenna Q-factor. Antenna assembly 10 has a magnetic dipole moment 35 in the plane perpendicular to the axis of elongation. The antenna dipole moment 35 is perpendicular to a line between the effective center of the magnet dipole moment 25 and the effective center of the antenna dipole moment. Thus, the antenna assembly 10 generates a RF magnetic field perpendicular to the magnetic field of the permanent magnet in the area in front of the probe in sensitive volume 24 which is defined by he magnetic field of the permanent magnet and the RF magnetic field parameters.

Specifically, the NMR excitation conditions exist where the static magnetic field has substantially equal magnitude corresponding to a particular RF magnetic field frequency, the RF magnetic field has a substantially equal amplitude related to the RF pulse duration and has a direction perpendicular to the static magnetic field. For the preferred embodiment of the probe presented in FIG. 2, the sensitive volume 24 is close to the shape of an arc in a cross-sectional plane perpendicular to the axis of elongation, the arc extending within a defined angle, typically 70–120 degrees, depending upon the particular geometry of the magnet and the RF antenna assembly. Since the volume of investigation 24 exists on one side of the probe of FIG. 2, it is referred to as a side looking NMR probe design. The preferred core material, however, can be utilized in applications other than side looking probes or NMR applications for formations adjacent a bore hole.

The preferred probe core uses a non ferrite powdered soft magnetic material core which exhibits a lower magnetic permeability than ferrite cores. The preferred powdered soft magnetic core material's permeability $\mu_m$ is typically 20–30, in contrast to permeability in the range of 500–1000, for ferrite NMR cores operating in the same frequency range. However, the preferred probe performs as effectively as a ferrite soft magnetic material as explained below.

For a given current in RF antenna elements 23 and 31, the antenna magnetic moment, and consequently the antenna RF magnetic field projected into the NMR volume of investigation 24 is proportional to the effective magnetic permeability $\mu$ of the preferred soft magnetic core. The effective magnetic permeability $\mu$ is calculated using the magnetic material permeability $\mu_m$ and a core demagnetizing factor, D as follows:

$$\mu = 1 + (\mu_m - 1)/((\mu_m - 1) \cdot D + 1)) \qquad (1)$$

The demagnetizing factor can be estimated from the elliptic equivalent of the cross-section of the core 22, as shown in FIG. 2, as follows:

$$D = S_x/(S_x + S_y) \qquad (2)$$

As shown in FIG. 2, in equation (2), Sx and Sy represent the elliptic equivalent dimensions in the horizontal and vertical dimensions respectively, in the plane of FIG. 2, for a preferred powdered soft magnetic material core 22 geometry. There are two limiting cases for equation (1), as follows:

$$(D)(\mu_m - 1) \ll 1 \text{ or } \mu \approx \mu_m; \text{ and} \qquad (3)$$

$$(D)(\mu_m - 1) \ll 1, \text{ which means } \mu \approx 1 + 1/D(\text{independent of } \mu_m). \qquad (4)$$

The second limit of equation (4) corresponds to the situation where the effective magnetic permeability and antenna efficiency are substantially independent of the magnetic permeability of the material. The maximum available permeability of the preferred, non-ferrite soft magnetic iron powder materials for the frequency around 1 MHz is about 20. If we require that D $(\mu_m - 1) > 5$, which means insignificant effective permeability loss compared to high permeability ferrite, then the effective permeability as defined by the equation (1) should be less than 5. This value for the effective permeability corresponds to the demagnetizing factor of more than 0.25 and the $S_y/S_x$ ratio of less than 3.

In a preferred embodiment, using the preferred powdered soft magnetic material, a magnetic core shape is provided, having values for $S_x$ and $S_y$, which ensure that the effective permeability of the core, $\mu$ as determined by the core proportions associated with the shape or core geometry does not exceed a value of 5. It is these relative proportions, rather than a particular shape that facilitate use of the preferred powdered core material. For known prior core geometric shapes, structure or designs, the effective magnetic permeability, dictated by the core shape, is greater than 5, which renders the preferred non ferrite powder soft magnetic material ineffective when compared to the performance of ferrite cores.

Figure 3:
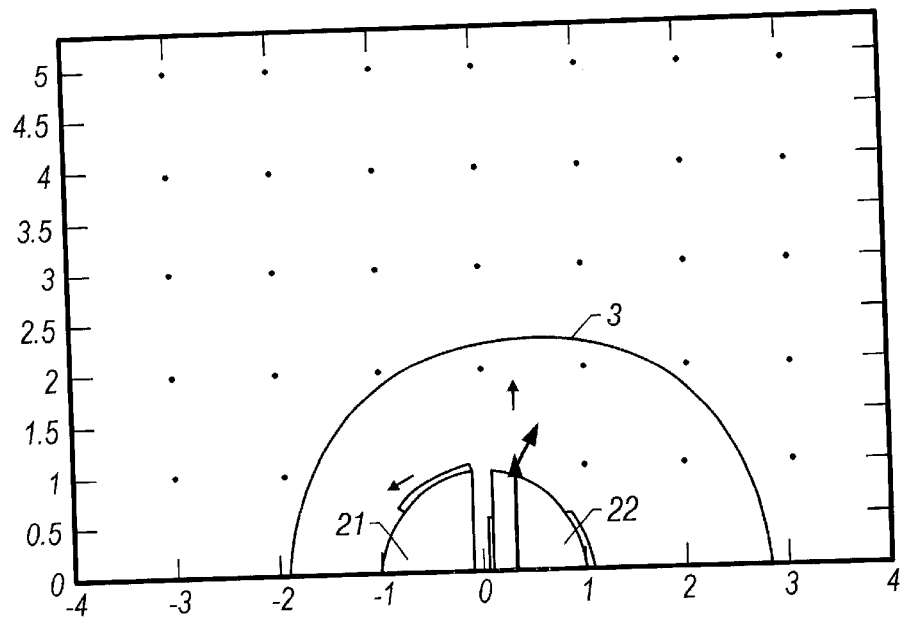
FIG. 3 is a plot of the isoline for the RF field generated by a preferred embodiment of the present invention utilizing a powdered soft magnetic core.
Figure 4:
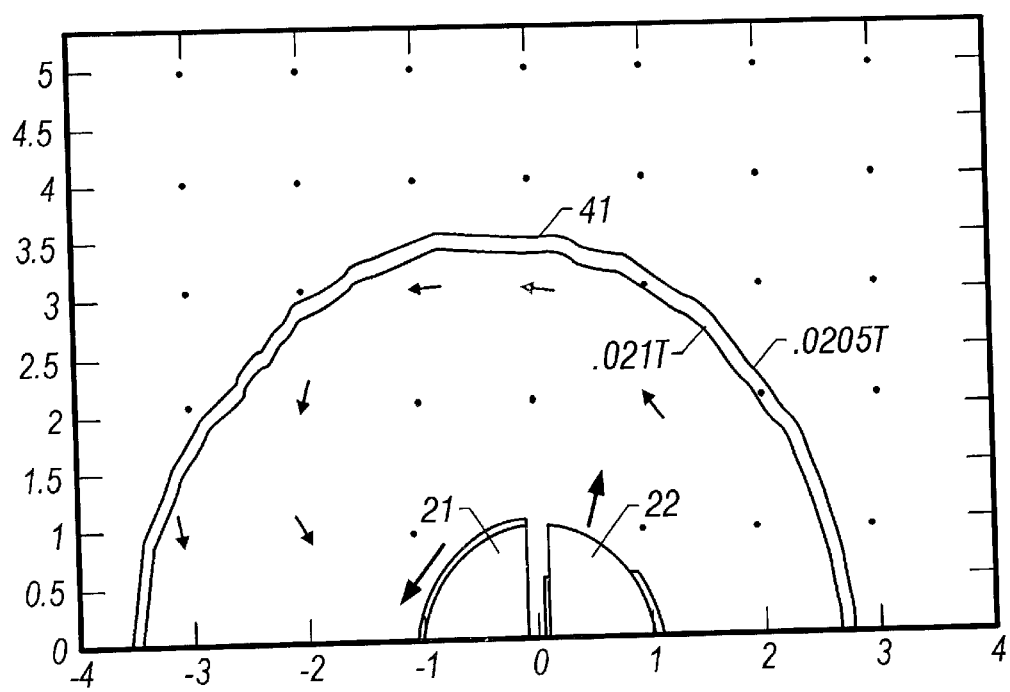
FIG. 4 is a plot of two isolines for the static field generated by a preferred embodiment of the present invention utilizing a powdered soft magnetic core.
Figure 5:
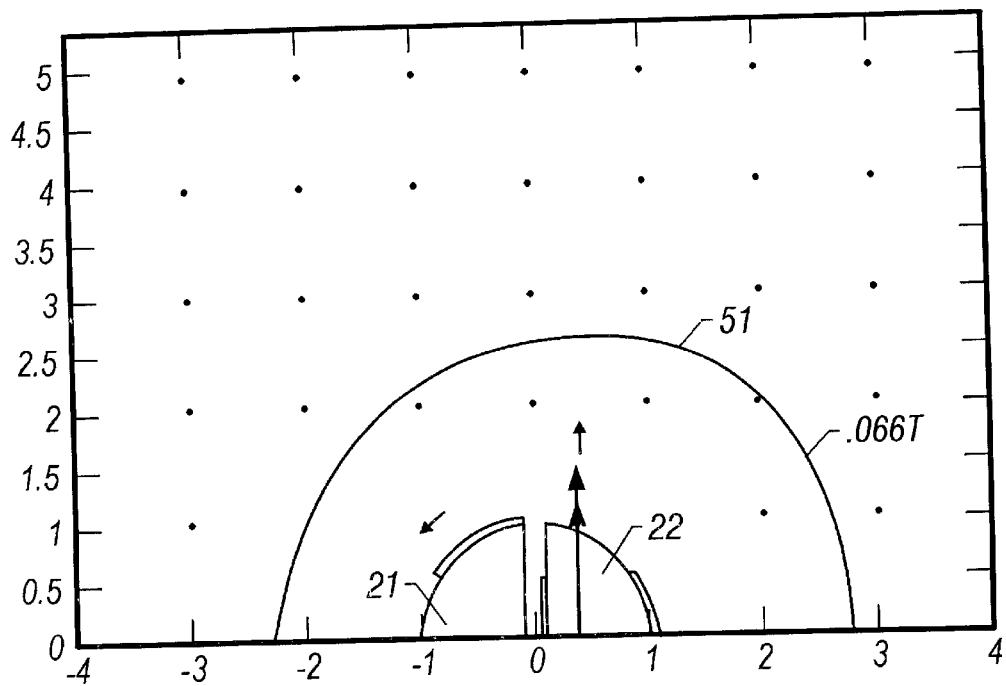
FIG. 5 is a plot of the isoline for the RF field generated by the probe geometry of FIG. 2 without utilizing a powdered soft magnetic core.
Figure 6:
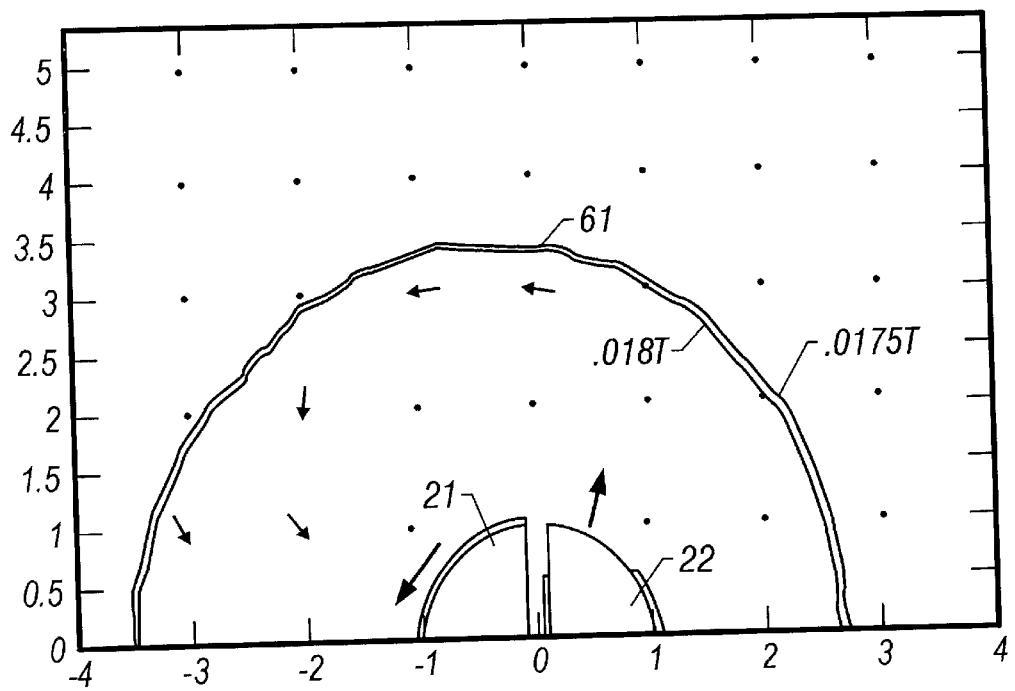
FIG. 6 is a plot of two isolines for the static field generated by the probe geometry of FIG. 1 without utilizing a powdered soft magnetic core.

FIG. 3 illustrates the isoline for the probe RF field when using the preferred soft magnetic material in the probe geometry of FIG. 2. FIG. 4 illustrates the isoline 41 for the static magnetic field, when using the preferred magnetic material in the core 22 of the preferred probe geometry of FIG. 2. The distances shown in FIGS. 3 and 4 are normalized to a NMR probe cross sectional radius of 2". Isolines for field strengths of 0.021 T and 0.0205 T are shown in FIG. 4. FIGS. 5 and 6 illustrate the isolines for the static magnetic field 51 and the RF magnetic field 61 respectively, for the probe geometry of FIG. 2, without using the preferred powdered soft magnetic material in core 22. Isolines for field strengths of 0.066 T are shown in FIG. 5 while isolines for a field strength of 0.018 T and 0.0175 T are shown in FIG. 6. Comparison of the static magnetic field and RF magnetic field isolines of FIGS. 3 and 4 to the static magnetic field and RF magnetic field isolines of FIGS. 5 and 6, demonstrates an improvement by a factor of 3 in the RF antenna efficiency and magnet field enhancement, for the probe design of FIG. 2 using the preferred powdered soft magnetic core material. Reciprocity principle suggests that the probe of FIG. 2, using a soft magnetic material core, provides a three-fold gain in probe sensitivity in the receiving mode as well.

Figure 7:
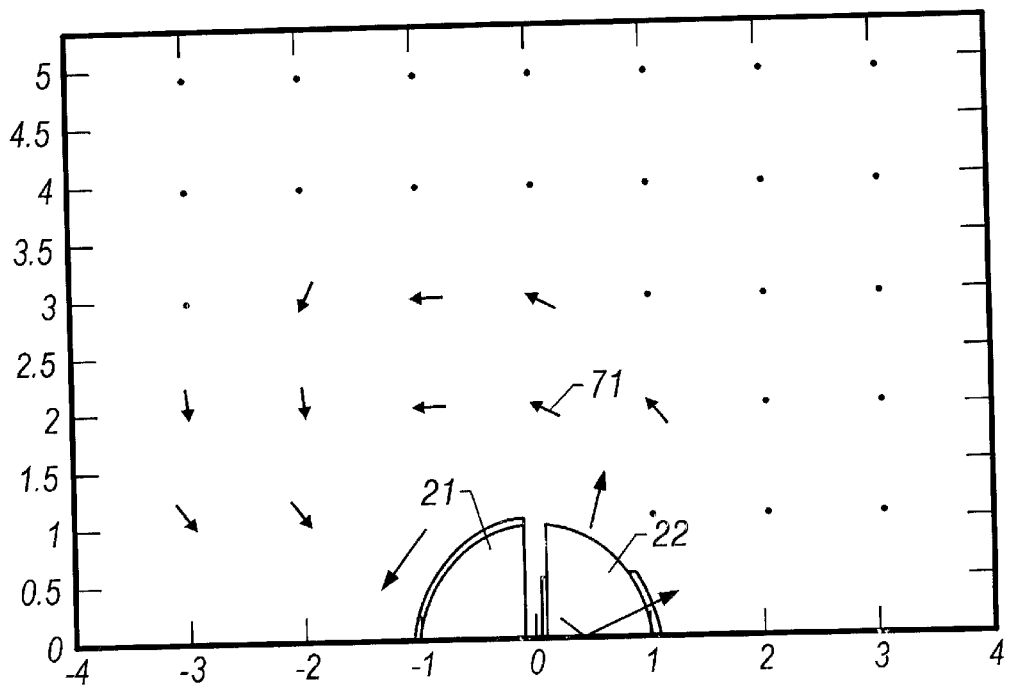
FIG. 7 illustrates the isolines for the magnetic flux density of the static field exceeding 0.35 T illustrating that no contour lines appear at the antenna core region.
Figure 8:
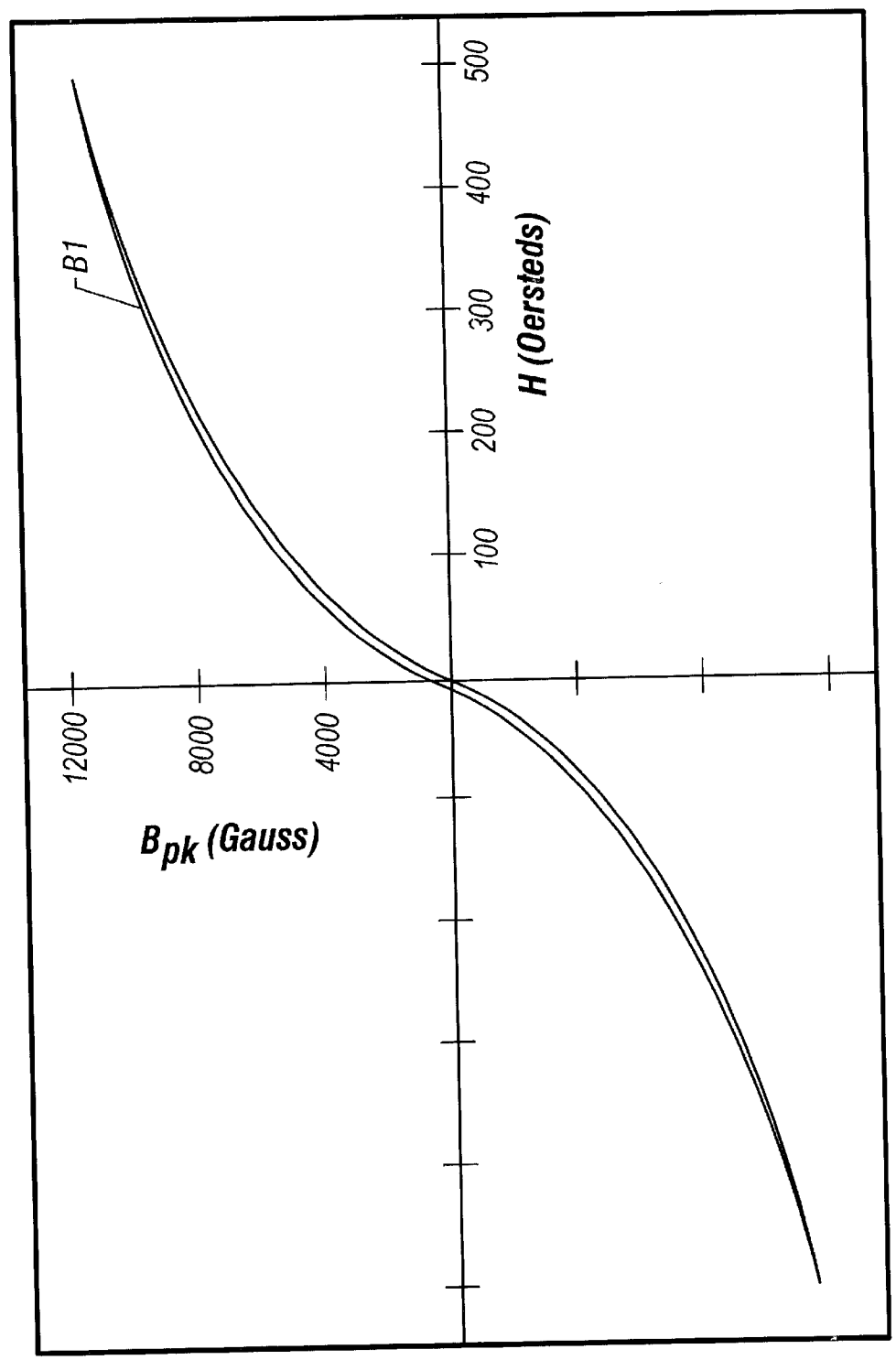
FIG. 8 illustrates the flux density value of 0.35 T as well below the saturation flux density of typical iron powdered soft magnetic materials.

FIG. 7 is a plot that was generated to show isolines for the magnetic flux density of the static magnetic field exceeding 0.35 T. None are seen. As it is clear from FIG. 8, presenting the magnetic hysteresis curve B1 for the preferred core material, the flux density value of 0.35 T is well below the saturation flux density of the preferred core soft magnetic iron powder materials which is about 1.2 T. This value typically exceeds the maximum flux density near the surface of the strongest permanent magnets (e.g., Sm2 Co17), thereby enabling a new variety of geometric core designs, not previously useful in core designs, which required compensation for the limitations of ferrite cores.

Figure 9:
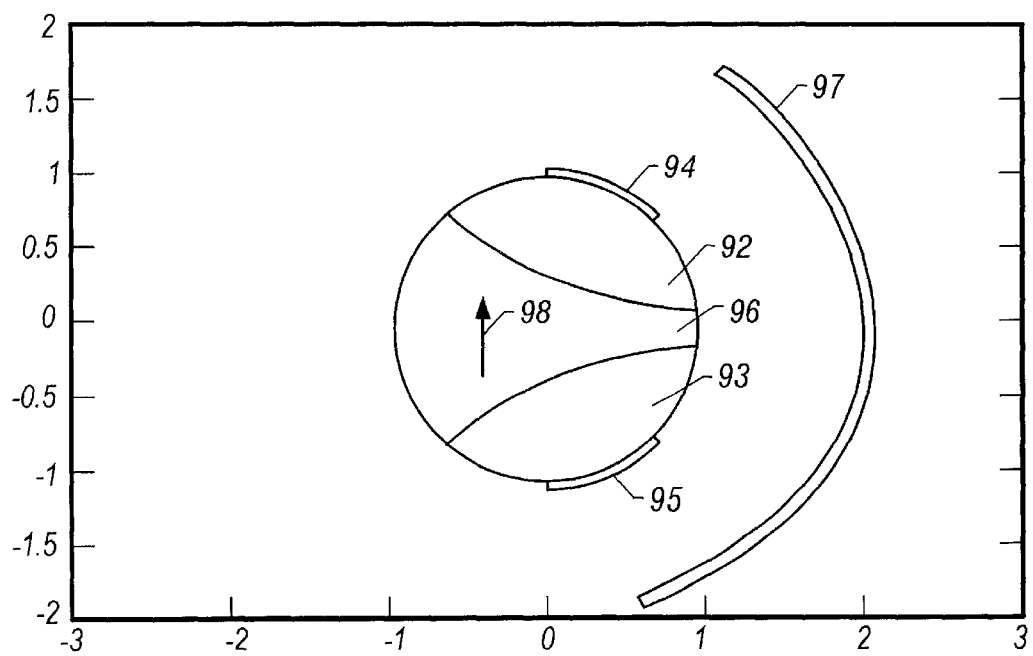
FIG. 9 is an illustration of an alternative embodiment of the present invention.

FIG. 9 illustrates an alternative embodiment of the present invention having two cores 92 and 93 and magnet 96. Antenna flat wires 94 and 95 are located adjacent cores 92 and 93, respectively. Magnet 96 has magnetic diphole 98. Preferably both cores are made of the preferred soft core material. The antenna assembly of FIG. 9 generates a RF magnetic field perpendicular to the magnetic field of the permanent magnet in the area in front of the probe in sensitive volume 97.

The limiting equations (1) and (2) and other geometric considerations, as well as the maximum effective permeability, as discussed in connection with use of the preferred powdered soft magnetic core material and core shape of FIG. 2, also apply to the alternative embodiment of the probe shown in FIG. 9.

In the preferred embodiment, as shown in FIG. 2, the antenna diphole moment is perpendicular to a line between an effective center of the magnet diphole moment and an effective center of the antenna diphole moment. In the alternative embodiment of FIG. 9, the permanent magnet has a magnetic diphole in a plane perpendicular to the axes of elongation and the antenna assembly has a dipole moment in a plane perpendicular to the axes of elongation and parallel to a line between the effective center of the magnet dipole moment and the effective center of the antenna dipole moment. In another alternative embodiment, the permanent magnet has a magnetic dipole moment in a plane perpendicular to the axes of elongation, the antenna assembly has a dipole moment in a plane perpendicular to the axes of elongation and the antenna dipole moment and the magnet dipole moment have coincident effective centers.

In addition to improving antenna efficiency, the flux concentration effect of the preferred powdered soft magnetic core provides the additional significant consequence of rendering the antenna assembly relatively insensitive to the conductivity of the permanent magnet. This insensitivity enables the use of relatively powerful conductive magnets, for example SmCo, to establish a larger static magnetic field, increasing the NMR signal and NMR signal-to-noise ratio.

The preferred powdered core material also reduces or substantially eliminates magnetostrictive ringing by virtue of the particulate structure of the preferred material. The magnetic particle size of the preferred core material (powder) is substantially smaller than the minimum wavelength for acoustic excitation associated with magnetostrictive ringing. Moreover, the epoxy binder does not efficiency transmit acoustic energy between particles.

The preferred powdered core magnetic and electrical characteristics are more stable than ferrite core characteristics in presence of temperature variations. This temperature stability is due to the fact that the magnetic and electrical characteristic of the preferred core is determined mainly by the shape of the core and the micro-geometry of the particulate structure (particle shape and volume packing density) of the preferred powdered material and substantially independent of the material of the particles.

What is claimed is:

1. A nuclear magnetic resonance sensing apparatus, comprising:
   a magnet for inducing a static magnetic field in materials to be analyzed; and
   an antenna assembly for inducing a radio frequency magnetic field within said materials and for detecting nuclear magnetic resonance signals from said materials, the antenna assembly comprising a coil and at least one magnetic core formed from a non-ferritic powdered soft magnetic material having high saturation flux density and a non-conductive bonding agent, said magnetic core having a magnetic permeability $\mu_m$ less than 500 and wherein said saturation flux density is greater than about 0.4 T.

2. The apparatus of claim 1, wherein, the magnetic core further comprising dimensions which are related to the direction of the RF magnetic field and to the magnetic permeability of the powdered soft magnetic material.

3. The apparatus of claim 1 wherein the powdered soft magnetic material is conductive and has a maximum grain size to substantially prevent intragranular power loss of said radio frequency magnetic field.

4. The apparatus of claim 1 wherein an effective demagnetizing factor of the magnetic core in a direction of the radio frequency magnetic field substantially exceeds the inverse magnetic permeability of the powdered soft magnetic material.

5. The apparatus of claim 4, wherein the core has an effective permeability, $\mu$, less than 5, as defined by a first equation, $$\mu = 1 + (\mu_m - 1)/((\mu_m - 1) \cdot D + 1),$$

wherein D, the demagnetizing factor can be estimated from an elliptic equivalent of the cross-section of the core, as defined by a second equation, $$D = S_x/(S_x + S_y),$$

wherein Sx and Sy represent the elliptic equivalent dimensions in horizontal and vertical dimensions respectively, in a plane the core.

6. The apparatus as defined in claim 1 wherein the magnet is made of a conductive permanent magnet material.

7. The apparatus as defined in claim 1 wherein the powdered soft magnetic material possesses a maximum magnetic permeability given a predetermined maximum RF antenna power loss.

8. The apparatus as defined in claim 1 wherein the magnet and the antenna possess an elongation direction, the radio frequency magnetic field and the static magnetic field being perpendicular to the elongation direction.

9. The apparatus of claim 1 wherein said flux density is greater than that of a magnetic consisting primarily of ferrite.

10. The apparatus of claim 1 wherein the magnetic core further comprises relative dimensions that are related to the direction of the RF magnetic field and to the magnetic permeability of the powdered soft magnetic material.

11. A probe, moveable through a bore hole for measuring nuclear magnetic resonance (NMR) properties in a volume of investigation in a formation surrounding a bore hole, comprising;

an elongated permanent magnet having an axis of elongation and a magnetic field perpendicular to the axis of elongation, the axis of elongation collinear with the bore hole; and an elongated antenna assembly having an axis of elongation generally parallel to the axis of the magnet, the permanent magnet and the antenna assembly disposed adjacent one another, the antenna assembly comprising at least one core comprising a non-ferritic powdered soft magnetic material having a magnetic permeability $\mu_m$ less than 500, said core having a saturation flux density greater than about 0.4 T, the antenna assembly generating a RF magnetic field substantially perpendicular to the magnetic field of the permanent magnet in the volume of investigation.

12. The probe of claim 11 wherein the permanent magnet has a magnetic dipole moment in a plane perpendicular to the axes of elongation, the antenna assembly comprising an elongated core placed in an antenna coil, the antenna coil having a coil dipole moment in a plane perpendicular to the axes of elongation, the coil dipole moment perpendicular to a line between an effective center of the magnet dipole moment and an effective center of the coil dipole moment.

13. The probe of claim 11, wherein the permanent magnet has a magnetic dipole moment in a plane perpendicular to the axes of elongation, the antenna assembly comprising two or more elongated cores placed in an antenna coil, the antenna coil having a coil dipole moment in a plane perpendicular to the axes of elongation, the coil dipole moment parallel to a line between an effective center of the magnet dipole moment and an effective center of the coil dipole moment.

14. The probe of claim 11, wherein the permanent magnetic has a magnetic dipole moment in a plane perpendicular to the axes of elongation, the antenna assembly comprising two or more elongated cores placed in an antenna coil, the antenna coil having a coil dipole moment in a plane perpendicular to the axes of elongation, the coil dipole moment and the magnet dipole moment having coincident effective centers.

15. A method of making measurements of a parameter of interest of materials to be analyzed comprising:
   using a magnet for inducing a static magnetic field in said materials; and
   using an antenna assembly for inducing a radio frequency magnetic field within said materials and for detecting nuclear magnetic resonance signals from said materials, the antenna assembly comprising a coil and at least one magnetic core formed from a non-ferritic powdered soft magnetic material having high saturation flux density and a non-conductive bonding agent, said magnetic core having a magnetic permeability $\mu_m$ less than 500 and a saturation flux density greater than about 0.4 T.

16. The method of claim 15 further comprising selecting dimensions for the magnetic core which are related to the direction of the direction of the RF magnetic field and to the magnetic permeability of the powdered soft magnetic material.

17. The method of claim 15 further comprising selecting relative dimensions for the magnetic core which are related to the direction of the direction of the RF magnetic field and to the magnetic permeability of the powdered soft magnetic material.

18. The method of claim 15 wherein the powdered soft magnetic material is conductive, the method further comprising selecting a maximum grain size for the soft magnetic material to substantially prevent intragranular power loss of said radio frequency magnetic field.

19. The method of claim 15 wherein an effective demagnetizing factor of the magnetic core in the direction of the direction of the radio frequency magnetic field substantially exceeds the inverse magnetic permeability of the powdered soft magnetic material.

20. The method of claim 19, wherein the core has an effective permeability, $\mu$, less than 5, as defined by a first equation, $$\mu=1+(\mu_m-1)/((\mu_m-1)\cdot D+1),$$

wherein D, the demagnetizing factor can be estimated from an elliptic equivalent of the cross-section of the core, as defined by a second equation, $$D=S_x/(S_x+S_y),$$

wherein Sx and Sy represent the elliptic equivalent dimensions in horizontal and vertical dimensions respectively, in a plane the core.

21. The method of claim 15, wherein the magnet is made of a conductive permanent magnet material.

22. The method of claim 15, wherein the powdered soft magnetic material possesses a maximum magnetic permeability given a predetermined maximum RF antenna power loss.

23. The method of claim 15, wherein the magnet and the antenna possess an elongation direction, the radio frequency magnetic field and the static magnetic field being perpendicular to the elongation direction.

24. A method of using a probe moveable through a bore hole for measuring nuclear magnetic resonance (NMR) properties of a volume of investigation in a formation surrounding the bore hole comprising:

using an elongated permanent magnet having an axis of elongation for providing a static magnetic field in the volume of investigation having a direction perpendicular to the axis of elongation, the axis of elongation collinear with the bore hole; and using an elongated antenna assembly on the probe for providing a radio frequency magnetic field in the volume of investigation having a direction substantially orthogonal to the static magnetic field, the antenna assembly having an axis of elongation generally parallel to the axis of the magnet, the permanent magnet and the antenna assembly disposed adjacent one another, the antenna assembly comprising at least one core comprising a non-ferritic powdered soft magnetic material said core having a magnetic permeability $\mu_m$ less than 500 and a saturation flux density greater than about 0.4 T.

25. The method of claim 24, the permanent magnet having a magnetic dipole moment in a plane perpendicular to the axes of elongation, the antenna assembly comprising an elongated core placed in an antenna coil, the antenna coil having a coil dipole moment in a plane perpendicular to the axes of elongation, the coil dipole moment perpendicular to a line between an effective center of the magnet dipole moment and an effective center of the coil dipole moment.

26. The method of claim 24, wherein the permanent magnet has a magnetic dipole moment in a plane perpendicular to the axes of elongation, the antenna assembly comprising two or more elongated cores placed in an antenna coil, the antenna coil having a coil dipole moment in a plane perpendicular to the axes of elongation, the coil dipole moment parallel to a line between an effective center of the magnet dipole moment and an effective center of the coil dipole moment.

27. The method of claim 24, wherein the permanent magnetic has a magnetic dipole moment in a plane perpendicular to the axes of elongation, the antenna assembly comprising two or more elongated cores placed in an antenna coil, the antenna coil having a coil dipole moment in a plane perpendicular to the axes of elongation, the coil dipole moment and the magnet dipole moment having coincident effective centers.

* * * * *